(12) United States Patent
Lorenzo et al.

(10) Patent No.: US 10,918,390 B2
(45) Date of Patent: Feb. 16, 2021

(54) HELICAL BALLOON ASSIST DEVICE AND METHOD FOR USING THE SAME

(71) Applicant: DePuy Synthes Products, Inc., Raynham, MA (US)

(72) Inventors: Juan Lorenzo, Raynham, MA (US); Kirk Johnson, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 214 days.

(21) Appl. No.: 15/941,166

(22) Filed: Mar. 30, 2018

(65) Prior Publication Data
US 2019/0298384 A1    Oct. 3, 2019

(51) Int. Cl.
| | | |
|---|---|---|
| *A61B 17/12* | (2006.01) | |
| *A61M 25/06* | (2006.01) | |
| *A61M 25/10* | (2013.01) | |
| *A61B 17/00* | (2006.01) | |

(52) U.S. Cl.
CPC .... *A61B 17/12136* (2013.01); *A61B 17/1204* (2013.01); *A61B 17/12036* (2013.01); *A61B 17/12109* (2013.01); *A61M 25/0662* (2013.01); *A61M 25/1002* (2013.01); *A61B 2017/00862* (2013.01); *A61B 2017/1205* (2013.01); *A61M 2025/0681* (2013.01)

(58) Field of Classification Search
CPC ....... A61B 17/12136; A61B 17/12022–12045; A61B 17/12109; A61B 17/22032; A61B 2017/22051; A61B 2017/22065–22071; A61B 2018/00285; A61M 25/0662; A61M 25/10–2025
See application file for complete search history.

(56) References Cited

U.S. PATENT DOCUMENTS

| | | | | |
|---|---|---|---|---|
| 3,811,448 A | * | 5/1974 | Morton | A61M 25/0017 604/102.02 |
| 4,762,130 A | * | 8/1988 | Fogarty | A61M 25/1002 606/159 |
| 5,181,911 A | * | 1/1993 | Shturman | A61M 25/104 604/103.07 |
| 5,226,888 A | * | 7/1993 | Arney | A61M 25/1002 604/103.07 |

(Continued)

FOREIGN PATENT DOCUMENTS

| | | |
|---|---|---|
| EP | 0 275 230 A2 | 7/1988 |
| WO | 2017/081561 A1 | 5/2017 |

OTHER PUBLICATIONS

European Search Report issued in corresponding European Patent Application No. 19 16 6286 dated Aug. 27, 2019.

*Primary Examiner* — Tan-Uyen T Ho
*Assistant Examiner* — Charles M Wei
(74) *Attorney, Agent, or Firm* — Troutman Pepper Hamilton Sanders LLP (57) ABSTRACT

The helical balloon assist device includes a tubular balloon formed at least partially into an independent helical shape in an uninflated state and an inflation tube in sealed communication with the balloon and extending from the helical balloon assist device in a proximal direction. The helical balloon assist device may include an inner core member formed at least partially into an independent helical shape and supporting the helical shape of the tubular balloon.

17 Claims, 6 Drawing Sheets

(56) References Cited

U.S. PATENT DOCUMENTS

| | | | | |
|---|---|---|---|---|
| 5,295,958 | A * | 3/1994 | Shturman | A61B 18/1492 604/103.07 |
| 5,554,119 | A * | 9/1996 | Harrison | A61M 16/0481 604/103.01 |
| 5,772,681 | A * | 6/1998 | Leoni | A61M 25/005 606/192 |
| 5,797,948 | A * | 8/1998 | Dunham | A61M 25/10 600/3 |
| 5,855,546 | A * | 1/1999 | Hastings | A61M 25/0127 600/3 |
| 6,196,996 | B1 * | 3/2001 | Teirstein | A61M 25/1002 600/3 |
| 6,391,037 | B1 | 5/2002 | Greenhalgh | |
| 6,398,708 | B1 | 6/2002 | Hastings et al. | |
| 6,409,652 | B1 * | 6/2002 | Kamdar | A61N 5/1002 600/3 |
| 7,081,115 | B2 * | 7/2006 | Taimisto | A61B 18/1492 606/41 |
| 7,766,871 | B2 * | 8/2010 | Hirszowicz | A61M 25/1002 604/103.07 |
| 8,079,978 | B2 | 12/2011 | Hirszowicz et al. | |
| 9,149,288 | B2 * | 10/2015 | Teague | A61B 17/22032 |
| 9,232,992 | B2 | 1/2016 | Heidner | |
| 9,532,792 | B2 | 1/2017 | Galdonik et al. | |
| 9,532,873 | B2 | 1/2017 | Kelley | |
| 9,533,344 | B2 | 1/2017 | Monetti et al. | |
| 9,539,011 | B2 | 1/2017 | Chen et al. | |
| 9,539,022 | B2 | 1/2017 | Bowman | |
| 9,539,122 | B2 | 1/2017 | Burke et al. | |
| 9,539,382 | B2 | 1/2017 | Nelson | |
| 9,549,830 | B2 | 1/2017 | Bruszewski et al. | |
| 9,554,805 | B2 | 1/2017 | Tompkins et al. | |
| 9,561,125 | B2 | 2/2017 | Bowman et al. | |
| 9,572,982 | B2 | 2/2017 | Burnes et al. | |
| 9,579,484 | B2 | 2/2017 | Barnell | |
| 9,585,642 | B2 | 3/2017 | Dinsmoor et al. | |
| 9,615,832 | B2 | 4/2017 | Bose et al. | |
| 9,615,951 | B2 | 4/2017 | Bennett et al. | |
| 9,622,753 | B2 | 4/2017 | Cox | |
| 9,636,115 | B2 | 5/2017 | Henry et al. | |
| 9,636,439 | B2 | 5/2017 | Chu et al. | |
| 9,642,675 | B2 | 5/2017 | Werneth et al. | |
| 9,655,633 | B2 | 5/2017 | Leynov et al. | |
| 9,655,645 | B2 | 5/2017 | Staunton | |
| 9,655,989 | B2 | 5/2017 | Cruise et al. | |
| 9,662,129 | B2 | 5/2017 | Galdonik et al. | |
| 9,662,238 | B2 | 5/2017 | Dwork et al. | |
| 9,662,425 | B2 | 5/2017 | Lilja et al. | |
| 9,668,898 | B2 | 6/2017 | Wong | |
| 9,675,477 | B2 | 6/2017 | Thompson | |
| 9,675,782 | B2 | 6/2017 | Connolly | |
| 9,676,022 | B2 | 6/2017 | Ensign | |
| 9,692,557 | B2 | 6/2017 | Murphy | |
| 9,693,852 | B2 | 7/2017 | Lam et al. | |
| 9,700,262 | B2 | 7/2017 | Janik et al. | |
| 9,700,399 | B2 | 7/2017 | Acosta-Acevedo | |
| 9,717,421 | B2 | 8/2017 | Griswold et al. | |
| 9,717,500 | B2 | 8/2017 | Tieu et al. | |
| 9,717,502 | B2 | 8/2017 | Teoh et al. | |
| 9,724,103 | B2 | 8/2017 | Cruise et al. | |
| 9,724,526 | B2 | 8/2017 | Strother et al. | |
| 9,750,565 | B2 | 9/2017 | Bloom et al. | |
| 9,757,260 | B2 | 9/2017 | Greenan | |
| 9,764,111 | B2 | 9/2017 | Gulachenski | |
| 9,770,251 | B2 | 9/2017 | Bowman | |
| 9,770,577 | B2 | 9/2017 | Li | |
| 9,775,621 | B2 | 10/2017 | Tompkins et al. | |
| 9,775,706 | B2 | 10/2017 | Peterson | |
| 9,775,732 | B2 | 10/2017 | Khenansho | |
| 9,788,800 | B2 | 10/2017 | Mayoras, Jr. | |
| 9,795,391 | B2 | 10/2017 | Saatchi et al. | |
| 9,801,980 | B2 | 10/2017 | Karino et al. | |
| 9,808,599 | B2 | 11/2017 | Bowman | |
| 9,833,252 | B2 | 12/2017 | Sepetka | |
| 9,833,604 | B2 | 12/2017 | Lam | |
| 9,833,625 | B2 | 12/2017 | Waldhauser et al. | |
| 10,286,184 | B2 * | 5/2019 | Laduca | A61M 25/0074 |
| 2002/0045925 | A1 * | 4/2002 | Keller | A61F 7/12 607/106 |
| 2005/0197667 | A1 * | 9/2005 | Chan | A61M 25/1025 606/194 |
| 2006/0064151 | A1 | 3/2006 | Guterman | |
| 2006/0287666 | A1 * | 12/2006 | Saadat | A61M 25/1011 608/198 |
| 2008/0281350 | A1 | 11/2008 | Sepetka | |
| 2009/0209969 | A1 * | 8/2009 | Wolfe | A61B 1/00071 606/108 |
| 2010/0145265 | A1 * | 6/2010 | Min | A61M 25/008 604/95.03 |
| 2010/0324649 | A1 | 12/2010 | Mattsson | |
| 2011/0144742 | A1 * | 6/2011 | Madrid | A61F 2/2433 623/2.11 |
| 2012/0226303 | A1 * | 9/2012 | Roche | A61M 25/104 606/194 |
| 2012/0245520 | A1 * | 9/2012 | Kelly | A61M 25/1002 604/103.09 |
| 2012/0283768 | A1 | 11/2012 | Cox et al. | |
| 2014/0135812 | A1 | 5/2014 | Divino et al. | |
| 2014/0135891 | A1 * | 5/2014 | Poehlmann | A61F 2/958 623/1.11 |
| 2014/0200607 | A1 | 7/2014 | Sepetka et al. | |
| 2014/0249506 | A1 * | 9/2014 | Laduca | A61F 2/958 604/509 |
| 2015/0238729 | A1 * | 8/2015 | Jenson | A61F 2/95 604/510 |
| 2017/0007264 | A1 | 1/2017 | Cruise et al. | |
| 2017/0007265 | A1 | 1/2017 | Guo et al. | |
| 2017/0020670 | A1 | 1/2017 | Murray et al. | |
| 2017/0020700 | A1 | 1/2017 | Bienvenu | |
| 2017/0027640 | A1 | 2/2017 | Kunis et al. | |
| 2017/0027692 | A1 | 2/2017 | Bonhoeffer | |
| 2017/0027725 | A1 | 2/2017 | Argentine | |
| 2017/0035436 | A1 | 2/2017 | Morita | |
| 2017/0035567 | A1 | 2/2017 | Duffy | |
| 2017/0042548 | A1 | 2/2017 | Lam | |
| 2017/0049596 | A1 | 2/2017 | Schabert | |
| 2017/0071737 | A1 | 3/2017 | Kelley | |
| 2017/0072452 | A1 | 3/2017 | Monetti et al. | |
| 2017/0079671 | A1 | 3/2017 | Morero et al. | |
| 2017/0079680 | A1 | 3/2017 | Bowman | |
| 2017/0079766 | A1 | 3/2017 | Wang | |
| 2017/0079767 | A1 | 3/2017 | Leon-Yip | |
| 2017/0079812 | A1 | 3/2017 | Lam et al. | |
| 2017/0079817 | A1 | 3/2017 | Sepetka | |
| 2017/0079819 | A1 | 3/2017 | Pung et al. | |
| 2017/0079820 | A1 | 3/2017 | Lam et al. | |
| 2017/0086851 | A1 | 3/2017 | Wallace | |
| 2017/0086996 | A1 | 3/2017 | Peterson et al. | |
| 2017/0095259 | A1 | 4/2017 | Tompkins et al. | |
| 2017/0100126 | A1 | 4/2017 | Bowman et al. | |
| 2017/0100141 | A1 | 4/2017 | Morero et al. | |
| 2017/0100143 | A1 | 4/2017 | Grandfield | |
| 2017/0100183 | A1 | 4/2017 | Iaizzo | |
| 2017/0113023 | A1 | 4/2017 | Steingisser et al. | |
| 2017/0147765 | A1 | 5/2017 | Mehta | |
| 2017/0151032 | A1 | 6/2017 | Loisel | |
| 2017/0165062 | A1 | 6/2017 | Rothstein | |
| 2017/0165065 | A1 | 6/2017 | Rothstein | |
| 2017/0165454 | A1 | 6/2017 | Tuohy | |
| 2017/0172581 | A1 | 6/2017 | Bose et al. | |
| 2017/0172766 | A1 | 6/2017 | Vong et al. | |
| 2017/0172772 | A1 | 6/2017 | Khenansho | |
| 2017/0189033 | A1 | 7/2017 | Sepetka et al. | |
| 2017/0189035 | A1 | 7/2017 | Porter | |
| 2017/0215902 | A1 | 8/2017 | Leynov et al. | |
| 2017/0216484 | A1 | 8/2017 | Cruise et al. | |
| 2017/0224350 | A1 | 8/2017 | Shimizu et al. | |
| 2017/0224355 | A1 | 8/2017 | Bowman et al. | |
| 2017/0224467 | A1 | 8/2017 | Piccagli et al. | |
| 2017/0224511 | A1 | 8/2017 | Dwork et al. | |
| 2017/0224953 | A1 | 8/2017 | Tran et al. | |
| 2017/0231749 | A1 | 8/2017 | Perkins et al. | |

(56) References Cited

U.S. PATENT DOCUMENTS

| | | |
|---|---|---|
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh |
| 2017/0303942 A1 | 10/2017 | Greenhalgh et al. |
| 2017/0303947 A1 | 10/2017 | Greenhalgh |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman |
| 2017/0333228 A1 | 11/2017 | Orth et al. |
| 2017/0333236 A1 | 11/2017 | Greenan |
| 2017/0333678 A1 | 11/2017 | Bowman |
| 2017/0340383 A1 | 11/2017 | Bloom et al. |
| 2017/0348014 A1 | 12/2017 | Wallace |
| 2017/0348514 A1 | 12/2017 | Guyon et al. |
| 2018/0014829 A1* | 1/2018 | Tal .................. A61B 17/12022 |

\* cited by examiner

HELICAL BALLOON ASSIST DEVICE AND METHOD FOR USING THE SAME

FIELD

This disclosure relates generally to the field of tools for vascular surgery. More particularly, it relates to balloon devices for occluding blood vessels during vascular surgery.

BACKGROUND

Balloon Guide Catheters facilitate the insertion of intravascular devices as well as control/restrict flow in ischemic applications. They are designed to have a large lumen to maximize clot capture, and are indicated for use as a conduit for clot retrieval devices. Because the balloon is an integral part of the assembly on these devices, the profile of the devices is very large, for example 8 F (2.7 mm) (French "F"=0.33 mm) as compared to a regular large ID guide catheter which might be sized 6 F (2.0 mm). Also, the overall flexibility of the system is decreased due to the required inflation lumen and dual layer construction needed to inflate the distal balloon. The combination of the large overall profile and the lack of distal flexibility makes tracking these devices in the neurovascular anatomy difficult. Accordingly, use of these devices is mostly limited to the proximal cerebral vasculature.

SUMMARY

To address these deficiencies in the existing art, a helical balloon assist device can include a tubular balloon formed at least partially into an independent helical shape in an uninflated state and an inflation tube in sealed communication with the balloon and extending from the helical balloon assist device in a proximal direction. The helical balloon assist device can also have an inner core member formed at least partially into an independent helical shape and supporting the helical shape of the tubular balloon. In examples, the inner core member may be formed of a resilient material.

Other examples have the inner core member secured to the balloon or secured to an interior portion of a balloon wall closest or farthest to a helical axis. The inner core member can be secured to a balloon wall by an adhesive, by welding, or by mechanical fastening. Other examples have the inner core member not secured to the balloon. The inner core member can be formed in a multiple helix shape with a second helix extending helically along a wall of the tubular balloon. Examples of the balloon include it being made of an elastic material or an inelastic material.

The helical balloon assist device can also have a positioner fabricated from a resilient material, and in certain examples, the positioner is the inflation tube. The positioner can be configured to position the helical balloon assist device in a radial direction.

The helical balloon assist device can be paired with a catheter system having a catheter and the helical balloon assist device, slidably engaging an outside of the catheter.

An exemplary method of using a helical balloon assist device can include the steps of deforming a distal turn of a balloon of the helical balloon assist device to create or expand a gap between turns of the balloon of the helical balloon assist device. Then inserting a catheter through the gap between the turns of the balloon, twisting the helical balloon assist device to fully mount the helical balloon assist device onto the catheter, and sliding the helical balloon assist device along the catheter, using an inflation tube or a positioner, to a treatment site in a patient's vasculature. The method can further include the steps of inflating the balloon of the helical balloon assist device using the inflation tube and then performing a clinical procedure. Afterwards, deflating the balloon of the helical balloon assist device using the inflation tube, and withdrawing the helical balloon assist device from the patient. In these examples, inflating the balloon of the helical balloon assist device causes at least a partial occlusion of a patient's blood vessel adjacent to the treatment site.

DETAILED DESCRIPTION

Figure 1:
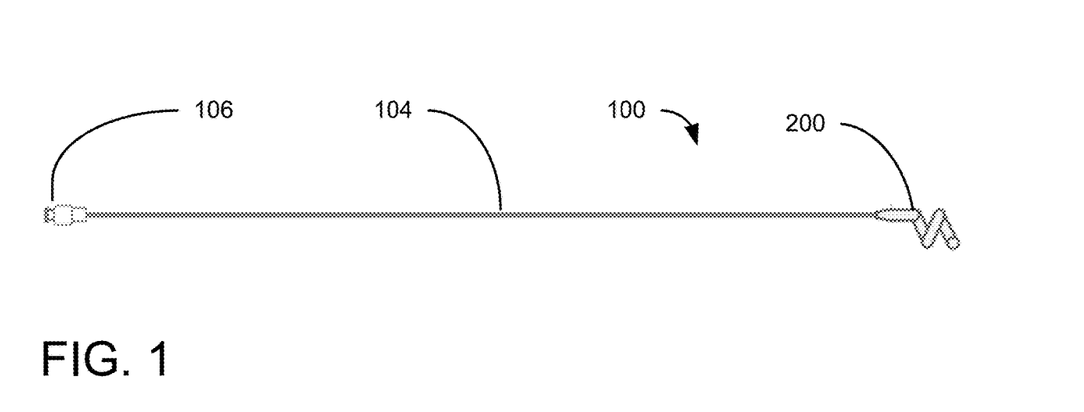
FIG. 1 is a diagram of the helical balloon assist device illustrating its basic components, in accordance with the present disclosure.
Figure 2:
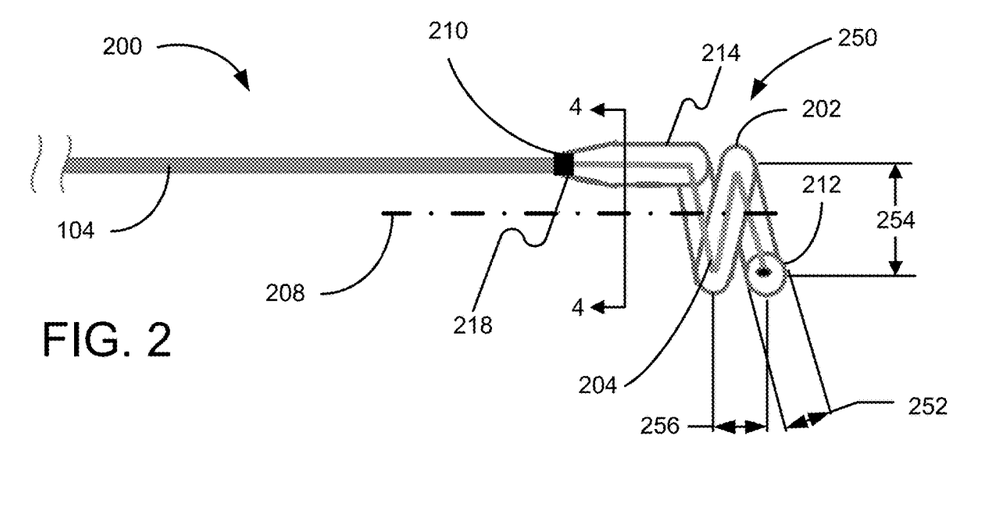
FIG. 2 is a diagram of the balloon assembly of the helical balloon assist device illustrating the balloon in the deflated state, in accordance with the present disclosure.
Figure 3:
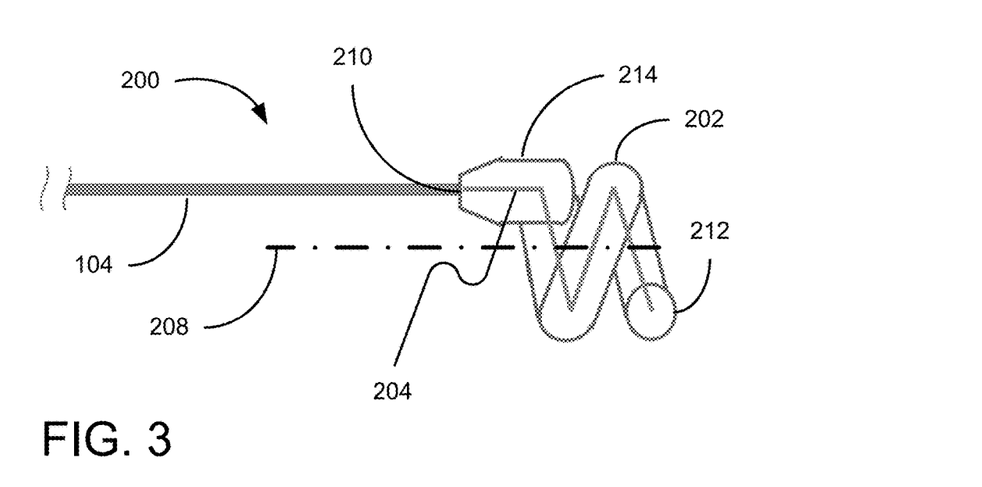
FIG. 3 is a diagram of the balloon assembly of the helical balloon assist device illustrating the balloon in the inflated state, in accordance with the present disclosure.

Referring now to the Figures, in which like reference numerals represent like parts, various examples of the helical balloon assist device and methods of using it will be disclosed in detail. FIG. 1 is a diagram of the helical balloon assist device illustrating is basic components. The helical balloon assist device 100 includes a balloon assembly 200, an inflation tube 104, and an inflation port 106. FIG. 2 is a closer view of the balloon assembly 200. The balloon assembly includes the balloon 202 supported by an inner core member 204. The balloon 202 can be formed from an elastic or semi-elastic material, like polyimide. The balloon 202 extends helically along and about an axis 208 from a proximal end 210 to a distal end 212. The inner core member 204 is a helical element supporting the balloon 202. In one example, the inner core member 204 may be a wire. Although a particular shape of the balloon 202 is illustrated, the disclosure is not limited to the shape shown.

The balloon 202 may have a straight section 214 at one or both ends which extends parallel to the axis 208. The straight section 214 may improve the robustness of the bond to the inflation tube 104, may improve the grip of the balloon 202 on a catheter 240, or may improve the ease of tracking the balloon 202 along the catheter 240. Alternatively, the balloon 202 may be purely helical. The helical portion 250 of the balloon 202 is described by a tube diameter 252, a nominal diameter 254 which defines the distance between the turns of the balloon 202 and the axis 208, and pitch 256 between turns of the balloon 202. The tube diameter 252 may be constant or variable. In some examples, the tube diameter 252 may taper toward the end 212 of the balloon 202. The pitch 256 may be constant or may be variable. In one example (not shown), the balloon 202 may have a "closed" end where a partial turn is non-helical, but instead has zero pitch and coils around the catheter following a plane perpendicular to the axis 208, similar to the "closed" end of a helical compression spring.

The balloon 202 is inflated using the inflation tube 104. Sterile water, saline, or another appropriate solution may be introduced to the inflation tube 104 at the inflation port 106. The inflation port 106 may be one of several types known in the industry. The inflation tube 104 has an open end 218 which terminates inside the balloon 202. The outer perimeter of the inflation tube 104 is bonded to balloon 202 at a location proximal to its open end 218. The bond provides a hermetic seal and a robust mechanical attachment to withstand forces during use of the helical balloon assist device 100.

The inflation tube 104 may be made from metal to facilitate pushability of the balloon 202 along the catheter 240, a polymeric material such as a polyimide for flexibility, or a combination of metal at the proximal end 210 and transitioning to the polymeric material as it extends toward the distal end 212. In some examples the inflation tube 104 may be used to position the helical balloon assist device 100 along the catheter 240 in the distal direction and to retract it in the proximal direction. In some examples, the inflation tube 104 may be attached to the inner core member 204. In other examples a separate positioner (not shown) may be attached to the balloon 202 and/or the inner core member 204 to advance the helical balloon assist device 100 along the catheter 240 in the distal direction and to retract it in the proximal direction, allowing the inflation tube 104 to be more flexible. The positioner may be made of a resilient material such as spring-temper stainless steel or, more preferably, Nitinol. In several examples the positioner may be attached by welding, for example by laser or ultrasonic means, by adhesive, by crimping, or by thermal staking, as may be appropriate depending on the materials of the positioner, the inner body 104, and/or the balloon 202.

A length L of the balloon assembly 200 may be relatively short in the axial direction. In one example, the balloon assembly 200 may be less than or equal to twice the outside diameter D of the catheter 240 (see, FIG. 6). In another example, the balloon assembly 200 may be less than or equal to the outside diameter D catheter 240. The short length L allows the balloon assembly 200 to track over tighter-radius bends of the catheter 240 which guides it.

Figure 4A:
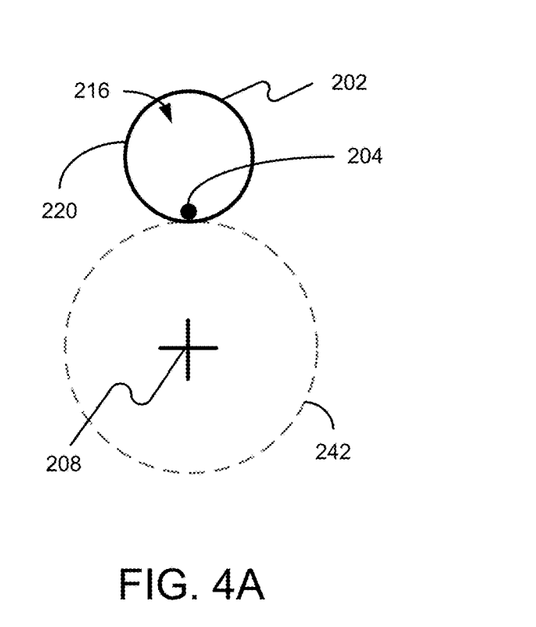
FIG. 4A is a cross-sectional diagram of the balloon assembly of the helical balloon assist device, illustrating one example of the inner core member positioned within the balloon close to the outside diameter of a catheter, in accordance with the present disclosure.
Figure 4B:
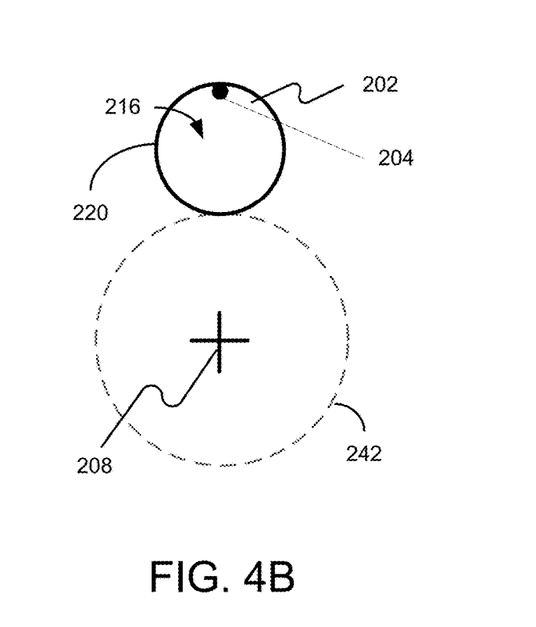
FIG. 4B is a cross-sectional diagram of the balloon assembly of the helical balloon assist device, illustrating one example of the inner core member positioned within the balloon far from the outside diameter of a catheter, in accordance with the present disclosure
Figure 4C:
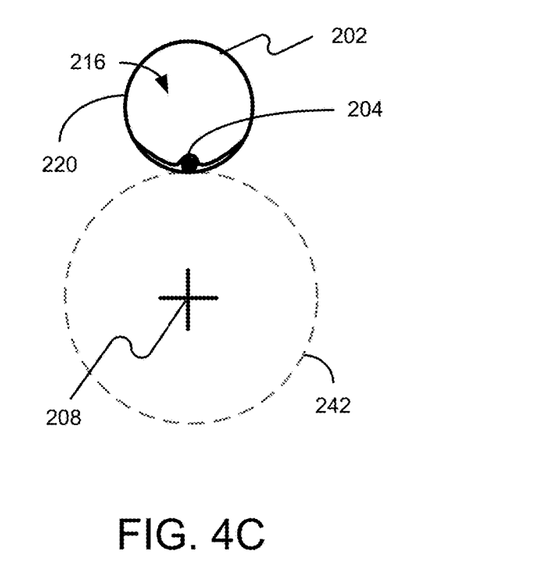
FIG. 4C is a cross-sectional diagram of the balloon assembly of the helical balloon assist device, illustrating one example of the inner core member positioned within the wall of the balloon, in accordance with the present disclosure

FIGS. 4A-4D illustrate examples of the inner core member 204. In one example, the inner core member 204 is made of a resilient material such as spring-temper stainless steel or, more preferably, a superelastic material such as Nitinol. The inner core member 204 has a helical shape which supports the balloon 202. The inner core member 204 may be secured to the balloon 202 or may be loose within the balloon 202. The inner core member 204 may be secured by an adhesive, by ultrasonic welding, by mechanical fasteners, by heat staking, or by other means known to those skilled in the art. If secured to the balloon 202, the inner core member 204 may be secured to the interior 216 of the balloon 202, the exterior of the balloon 202, or within a wall 220 of the balloon 202, as shown in FIG. 4C. The inner core member 204 may also be secured to the inflation tube 104 by an adhesive, by ultrasonic welding, by mechanical fasteners, by heat staking, or by other means known to those skilled in the art. In one example, the inner core member 204 may be formed into a helix following the wall 220 of the balloon 202 closest to the catheter 240, i.e., a helix having a nominal diameter similar to the outer diameter 242 of the catheter 240 as shown in FIG. 4A. In another example, the inner core member 204 may be formed into a helix following the wall 220 of the balloon 202 farthest to the catheter 240 as shown in FIG. 4B, i.e., a helix having a nominal diameter approximately equal to the outer diameter D (illustrated by a circumference 242) of the catheter 240 plus twice the tube diameter of the balloon 202.

Figure 4D:
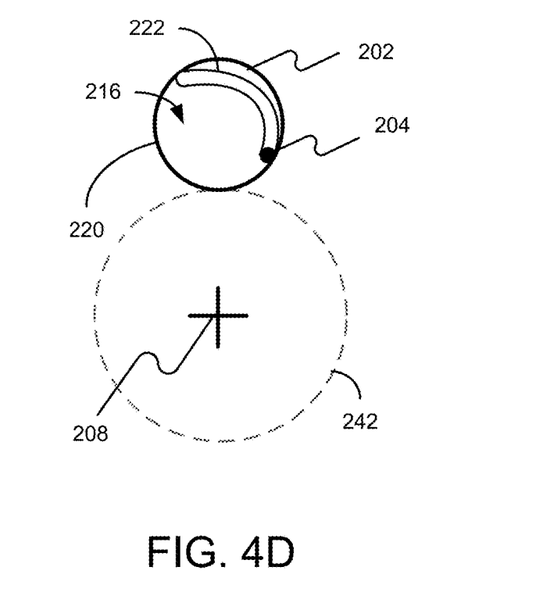
FIG. 4D is a cross-sectional diagram of the balloon assembly of the helical balloon assist device, illustrating one example of the inner core member positioned within the balloon, in a multiple-helix shape, in accordance with the present disclosure.

In another example, the inner core member 204 may be formed into a multiple helix 222 which helically follows the inside wall 220 of the helical shape of the balloon 202 as shown in FIG. 4D. The multiple helix 222 has a nominal diameter approximately equal to the tube diameter of the balloon and winds helically along an axis approximating a spline following the center of the balloon tube. Thus, the multiple helix 222 resembles a long coil spring wrapped around the catheter 240. The multiple helix 222 may be formed, for example, mechanically or by heat-treating the inner core member 204 on a form.

Figure 5:
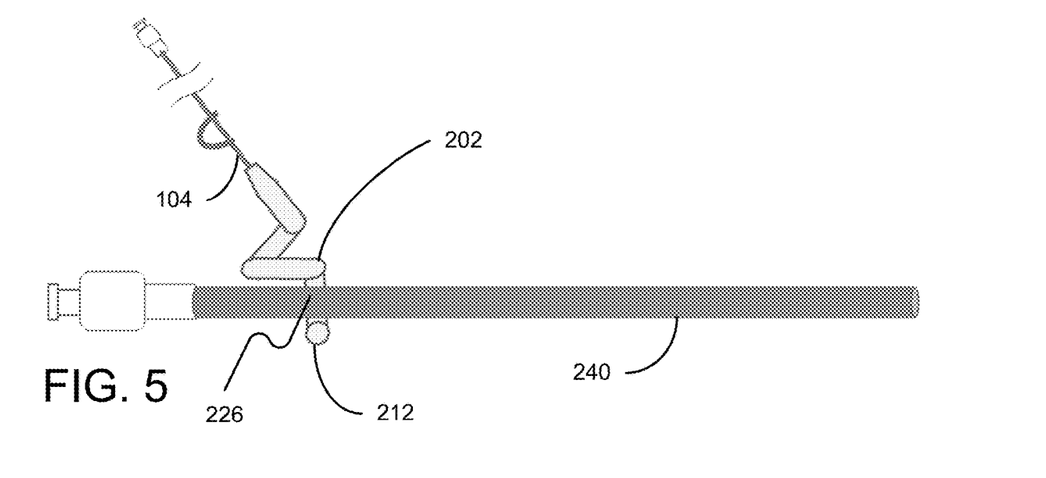
FIG. 5 is a diagram of mounting the helical balloon assist device on the proximal end of the catheter body, in accordance with the present disclosure.
Figure 6:
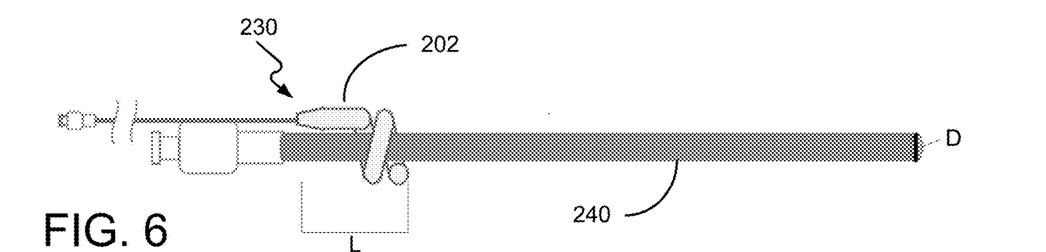
FIG. 6 is a diagram of mounting the helical balloon assist device fully mounted on the proximal end of the catheter body, in accordance with the present disclosure.
Figure 7:
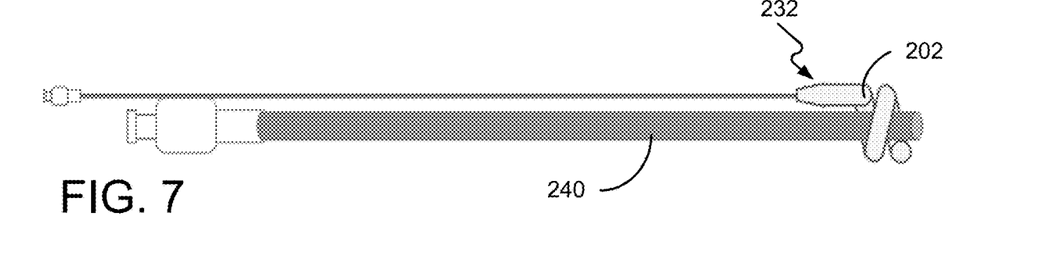
FIG. 7 is a diagram of the helical balloon assist device mounted on the catheter body and positioned at the distal end of the catheter, in accordance with the present disclosure.
Figure 8:
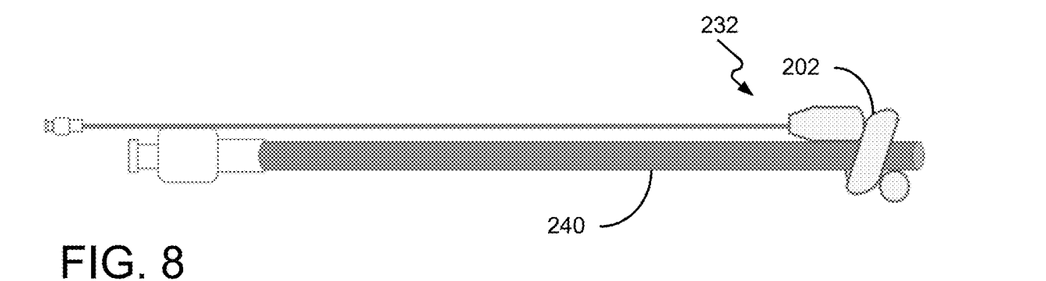
FIG. 8 is a diagram of the helical balloon assist device balloon inflated at the distal end of the catheter, in accordance with the present disclosure.

FIGS. 5-8 show the basic operation of the helical balloon assist device 100. FIG. 5 shows the balloon assist device being temporarily deformed and mounted on the catheter by twisting in a corkscrew fashion. The distal end 212 of the balloon 202 is deformed to create a gap 226 between the distal-most turn of the balloon 202 and the next-most distal turn. FIG. 6 shows the helical balloon assist device fully mounted on the catheter in a proximal position 230. The helical balloon assist device 100 is then slid along the catheter 240 using the inflation tube 104 or a separate positioner (not shown). FIG. 7 shows the helical balloon assist device 100 mounted on the catheter 240 in the distal position 232 after sliding along the catheter 240. The balloon 202 is then inflated using the inflation tube 104, as shown in FIG. 8.

Figure 9:
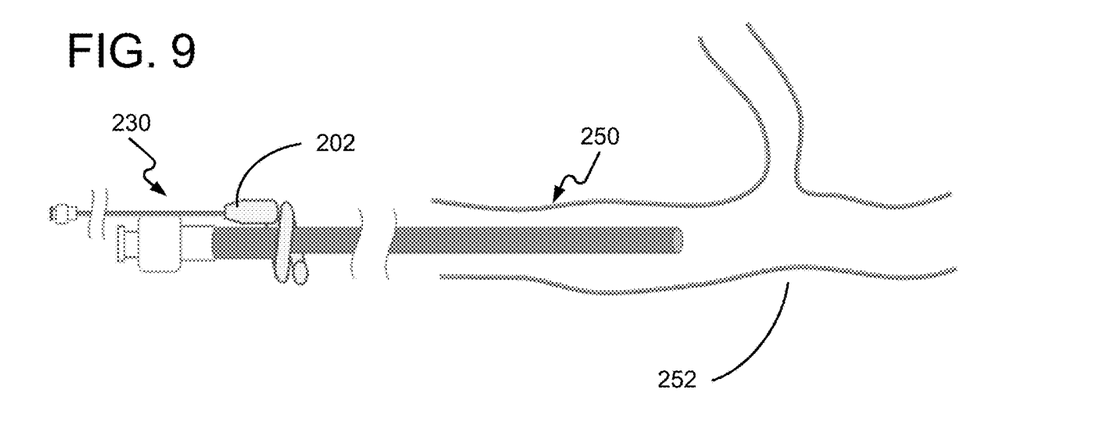
FIG. 9 is a diagram of a catheter positioned in a patient's vasculature with the helical balloon assist device mounted to the proximal end of the catheter body, in accordance with the present disclosure.
Figure 10:
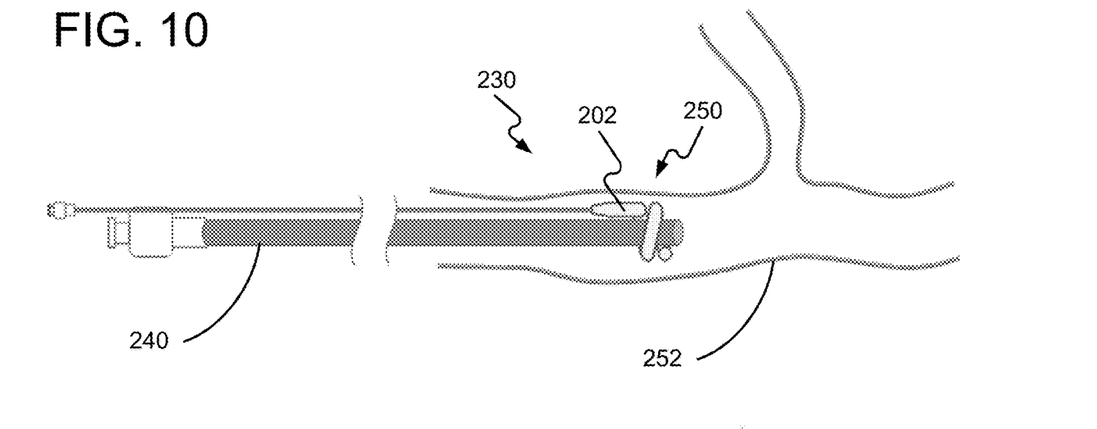
FIG. 10 is a diagram of a catheter positioned in a patient's vasculature with the helical balloon assist device positioned on the distal end of the catheter body at the treatment site, in accordance with the present disclosure.
Figure 11:
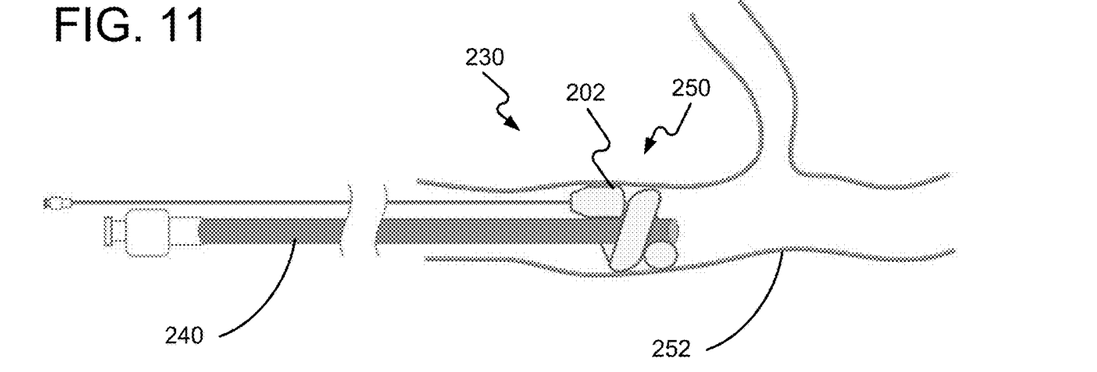
FIG. 11 is a diagram of a catheter positioned in a patient's vasculature with the balloon inflated at the treatment site, occluding a blood vessel, in accordance with the present disclosure.

FIGS. 9-11 show the basic operation of the helical balloon assist device 100 during a medical procedure. FIG. 9 shows the helical balloon assist device 100 fully mounted in the proximal position 230 on a catheter 240 which a clinician may have already positioned at a treatment site 250 within a patient's vasculature 252. The helical balloon assist device 100 is then slid along the catheter 240 using the inflation tube 104 or a separate positioner (not shown) to treatment site 250. FIG. 10 shows the helical balloon assist device 100 mounted on the catheter 240 in the distal position 232 at the treatment site 250. The balloon 202 is then inflated using the inflation tube 104 to occlude part of the patient's vasculature 252, as shown in FIG. 11. In some examples, helical balloon assist device 100 may be used during a clinical procedure to occlude blood flow, to occlude or capture tissue, plaques, or debris liberated by the procedure, or to hold the catheter 240 in position in the blood vessel.

Figure 12:
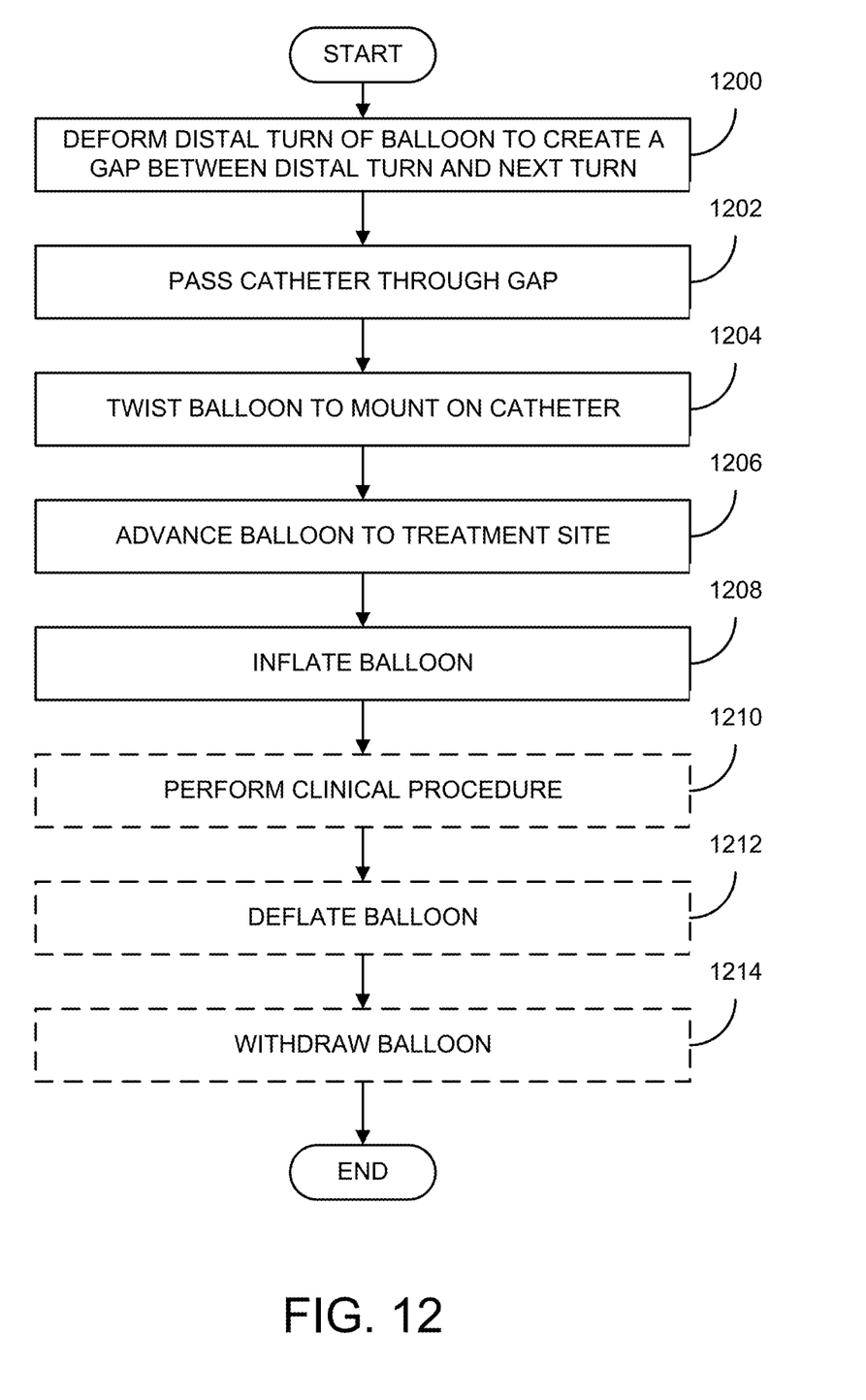
FIG. 12 is a flow chart illustrating one example of a method for using the helical balloon assist device, in accordance with the present disclosure.

FIG. 12 is flow chart showing the steps for using the helical balloon assist device 100. At 1200 the distal end of the balloon is deformed to create or expand a gap 226 between turns of the helix. At 1202 the catheter 240 is inserted through the gap 226 between the turns of the balloon 202. At 1204 the helical balloon assist device 100 is twisted fully onto the catheter 240 in a corkscrew fashion. At 1206 the inflation tube 104 or a positioner is used to slide the helical balloon assist device 100 along the catheter 240 to a treatment site 250 in a patient's vasculature 252. In some examples the positioner may be the inflation tube 104. At 1208 the helical balloon assist device 100 is inflated at the treatment site 250 using the inflation tube 104. The remaining steps are optional based on the clinical procedure. At 1210 a procedure is performed while the inflated helical balloon assist device 100 occludes a blood vessel at the treatment site 250. At 1212 the helical balloon assist device 100 is deflated. At 1214 the deflated helical balloon assist device 100 is withdrawn.

To facilitate an understanding of the principals and features of the disclosed technology, illustrative examples are explained above. The components described hereinafter as making up various elements of the disclosed technology are intended to be illustrative and not restrictive. Many suitable components that would perform the same or similar functions as components described herein are intended to be embraced within the scope of the disclosed devices and methods. Such other components not described herein may include, but are not limited to, for example, components developed after development of the disclosed technology.

Although the examples describe mounting the helical balloon assist device on a catheter, it may similarly be employed with a guidewire, lumen, or any similarly elongated vascular surgical tool.

It must also be noted that, as used in the specification and the appended claims, the singular forms "a," "an" and "the" include plural referents unless the context clearly dictates otherwise. By "comprising" or "containing" or "including" is meant that at least the named component or method step is present in the article or method, but does not exclude the presence of other components or method steps, even if the other such components or method steps have the same function as what is named.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

The design and functionality described in this application is intended to be exemplary in nature and is not intended to limit the instant disclosure in any way. Those having ordinary skill in the art will appreciate that the teachings of the disclosure may be implemented in a variety of suitable forms, including those forms disclosed herein and additional forms known to those having ordinary skill in the art.

Certain examples of this technology are described above with reference to flow diagrams. Some blocks of the block diagrams and flow diagrams may not necessarily need to be performed in the order presented, or may not necessarily need to be performed at all, according to some examples of the disclosure.

While certain examples of this disclosure have been described in connection with what is presently considered to be the most practical and various examples, it is to be understood that this disclosure is not to be limited to the disclosed examples, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain examples of the technology and also to enable any person skilled in the art to practice certain examples of this technology, including making and using any apparatuses or systems and performing any incorporated methods. The patentable scope of certain examples of the technology is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A helical balloon assisted catheter system comprising:
a catheter; and
a helical balloon assist device, slidably contacting an outside of the catheter, the helical balloon assist device comprising:
a tubular balloon formed at least partially into an independent helical shape in an uninflated state,
a distalmost end of the tubular balloon slidably contacting the outside of the catheter,
the helical shape comprises a plurality of turns defining an inner diameter of the helical shape, the inner diameter being consistent along at least a majority of the length of the helical shape, and
at least a portion of the turns are movable to resize a gap between adjacent turns in the plurality of turns; and
an inflation tube in sealed communication with the balloon and extending from a proximal end of the balloon in a proximal direction along the outside of the catheter.

2. The helical balloon assisted catheter system of claim 1, wherein the helical balloon assist device further comprises an inner core member formed at least partially into an independent helical shape and supporting the helical shape of the tubular balloon.

3. The helical balloon assisted catheter system of claim 2 where the inner core member is formed of a resilient material.

4. The helical balloon assisted catheter system of claim 2 where the inner core member is secured to the balloon.

5. The helical balloon assisted catheter system of claim 4 where the inner core member is secured to an interior portion of a balloon wall closest to a helical axis.

6. The helical balloon assisted catheter system of claim 4 where the inner core member is secured to an interior portion of a balloon wall farthest to a helical axis.

7. The helical balloon assisted catheter system of claim 4 where the inner core member is secured to a balloon wall by an adhesive, by welding, or by mechanical fastening.

8. The helical balloon assisted catheter system of claim 2 where the inner core member is formed in a multiple helix shape comprising a second helix extending helically along a wall of the tubular balloon.

9. The helical balloon assisted catheter system of claim 2 where the inner core member is not secured to the balloon.

10. The helical balloon assisted catheter system of claim 1 where the balloon comprises an elastic material.

11. The helical balloon assisted catheter system of claim 1 where the balloon comprises an inelastic material.

12. The helical balloon assisted catheter system of claim 1 further comprising a positioner fabricated from a resilient material.

13. The helical balloon assisted catheter system of claim 12 where the positioner comprises the inflation tube.

14. The helical balloon assisted catheter system of claim 12 where the positioner is configured to position the balloon in a distal direction and a proximal direction.

15. A helical balloon assisted catheter system comprising:
a catheter; and
a helical balloon assist device, slidably contacting an outside of the catheter, comprising:
  a tubular balloon formed at least partially into an independent helical shape in an uninflated state, a distalmost end of the tubular balloon slidably contacting the outside of the catheter, and
  an inflation tube in sealed communication with the balloon and extending from the balloon in a proximal direction along the outside of the catheter.

16. The balloon assisted catheter system of claim 15 further comprising a positioner pushable to move the balloon in a distal direction and pullable to move the balloon in a proximal direction along the catheter.

17. The balloon assisted catheter system of claim 15 further comprising an inner core member formed at least partially into an independent helical shape and supporting the helical shape of the tubular balloon.

* * * * *